(12) United States Patent
Toth

(10) Patent No.: US 6,866,419 B2
(45) Date of Patent: Mar. 15, 2005

(54) METHODS AND APPARATUS FOR MOTION CORRECTION IN IMAGING SYSTEMS

(75) Inventor: Thomas L. Toth, Brookfield, WI (US)

(73) Assignee: GE Medical Systems Global Technology Company LLC, Waukesha, WI (US)

(*) Notice: Subject to any disclaimer, the term of this patent is extended or adjusted under 35 U.S.C. 154(b) by 205 days.

(21) Appl. No.: 10/249,056

(22) Filed: Mar. 12, 2003

(65) Prior Publication Data

US 2004/0179652 A1 Sep. 16, 2004

(51) Int. Cl.$^7$ .............................................. G01D 18/00
(52) U.S. Cl. ................................ 378/207; 378/205
(58) Field of Search ............................ 378/4, 19, 205, 378/207

(56) References Cited

U.S. PATENT DOCUMENTS

| | | | |
|---|---|---|---|
| 5,550,889 A | 8/1996 | Gard et al. | 378/113 |
| 5,706,326 A | 1/1998 | Gard | 378/19 |
| 6,185,275 B1 | 2/2001 | Toth et al. | 378/113 |
| 6,322,248 B1 * | 11/2001 | Yanagita et al. | 378/205 |
| 6,370,218 B1 | 4/2002 | Toth et al. | 378/19 |
| 6,385,279 B1 | 5/2002 | Toth et al. | 378/11 |

* cited by examiner

Primary Examiner—David V. Bruce
Assistant Examiner—Courtney Thomas
(74) Attorney, Agent, or Firm—Carl B. Horton, Esq.; Armstrong Teasdale LLP

(57) ABSTRACT

A method for facilitating a reduction in image artifacts includes determining at least one error due to motion of an imaging system relative to a scan space, scanning an object to acquire data with the imaging system, and correcting the acquired data using the determined error.

28 Claims, 5 Drawing Sheets

Beam movement error in X relative to space mount pin on collimator
•use inner rows (1,2) to compute centroid in each view

METHODS AND APPARATUS FOR MOTION CORRECTION IN IMAGING SYSTEMS

BACKGROUND OF INVENTION

This invention relates to computed tomographic (CT) imaging, and more particularly to methods and apparatus for motion correction.

Recent advancements in CT technology (faster scanning speed, larger coverage with multiple detector rows) have lead to new engineering challenges. For example, the latest technology multislice scanners employ increased scan speeds (0.5 second per revolution or less) and isotropic resolution (0.5 mm or less in X, Y, and Z) to support high resolution 3D clinical applications. Reducing artifacts in reconstructed images is one such engineering challenge. Specifically, reducing motion artifacts is desirable. For example, a method for correction of focal spot motion caused by thermal drift is described by Toth et al. in U.S. Pat. No. 6,185,275. However, this is a method that only corrects the projection data for the mean X axis position over a gantry rotation cycle. View to view position errors as a function of rotation angle or errors due to other factors are not corrected. Other methods to measure and adjust the X-axis position of the focal spot are described by Gard in U.S. Pat. No. 5,706,326 and Gard et al. in U.S. Pat. No. 5,550,889. Methods to measure and adjust the Z-axis position of the X-ray beam on the detector are also described by Toth et al. in U.S. Pat. No. 6,370,218 and Toth et al. in U.S. Pat. No. 6,385,279. However, the errors addressed by all the above methods are relative to the gantry system and not relative to the scan space. Hence, errors due to movement of the gantry system relative to the object being scanned are not corrected.

SUMMARY OF INVENTION

In one aspect, a method for facilitating a reduction in image artifacts is provided. The method includes determining at least one error due to motion of an imaging system relative to a scan space, scanning an object to acquire data with the imaging system, and correcting the acquired data using the determined error.

In another aspect, an imaging system is provided. The imaging system includes a radiation source, a radiation source positioned to define a scan space between the detector and the source, and a computer is operationally coupled to the radiation source and the radiation detector. The computer is configured to scan an object to acquire data, determine a current status of at least one operating parameter including at least one of a temperature, a gantry angle, and a Z-position during the scan, and correct the acquired data for motion relative to a scan space using the determined current status of the operating parameter.

In yet another aspect, a product line of imaging systems is provided. The product line includes a plurality of imaging systems each including a radiation detector, a radiation source positioned to define a scan space between the detector and the source, and a computer operationally coupled to the detector and the source. Each imaging system is configured to correct for motion relative to the scan space using stored errors particular to that imaging system.

In still another aspect, a computer is provided. The computer is configured to scan an object to acquire data, and determine a current status of at least one operating parameter including at least one of a temperature, a gantry angle, and a Z-position during the scan, and correct the acquired data for motion relative to a scan space using the determined current status.

In another aspect, a computer readable medium encoded with a program configured to instruct a computer is provided. The program is configured to instruct the computer to determine a current status of at least one operating parameter of an imaging system including at least one of a temperature, a gantry angle, and a Z-position during a scan which acquires data, and correct the acquired data for motion relative to a scan space using the determined current status.

In yet another aspect, a method for determining misalignment is provided. The method includes determining at least one error due to motion of an imaging system relative to a scan space, comparing the determined error to a reference scan space, and providing an indication of misalignment when the determined error exceeds the reference value.

DETAILED DESCRIPTION

Figure 1:
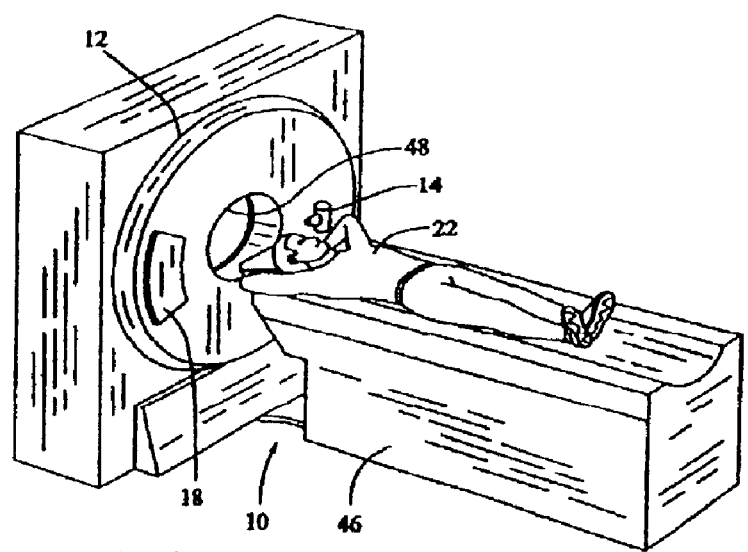
FIG. 1 is a pictorial view of an imaging system.

The methods and apparatus described herein address the detection and correction of motion induced errors between an imaging system and a scan space between a radiation detector and a radiation source. As explained in greater detail below, imaging systems have a plurality of operating parameters such as temperature, gantry angle, and Z-location. By discerning motion errors associated with these different parameters, image data is correctable when a scan is performed where the current parameters are determined. Once the current statuses of the operating parameters are determined, the motion errors associated with those parameters are used to facilitate a reduction of artifacts in reconstructed images. For example, a particular system has error 1 when cold and error 2 when hot, and while a scan is performed on an object of interest, the system determines whether the system is hot or cold and corrects accordingly. In another example, and because the correction is system specific, a particular system with no error when cold and error 3 when hot only applies error correction when scanning while hot.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a helical scan may be performed. To perform a helical scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix set of cone beam projection data. Similar to the single slice helical weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
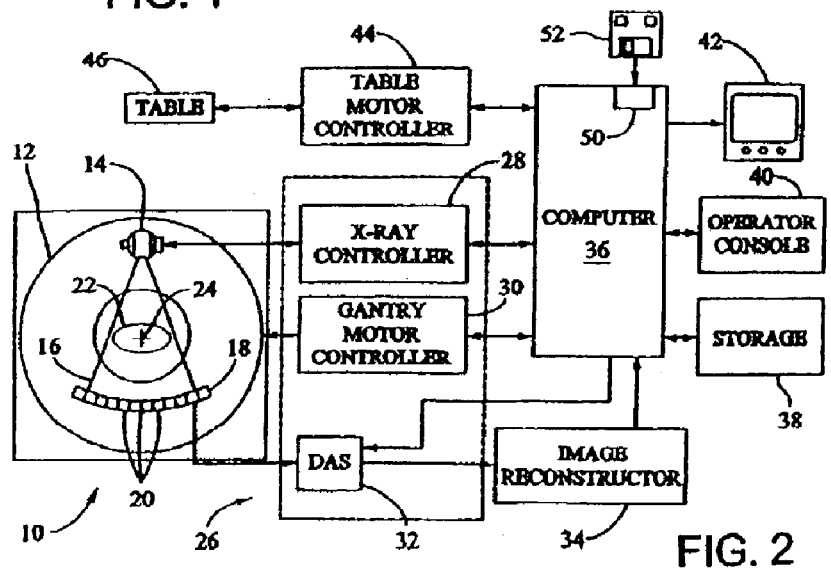
FIG. 2 is a block schematic diagram of the system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 situated in a scan space 23 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 3:
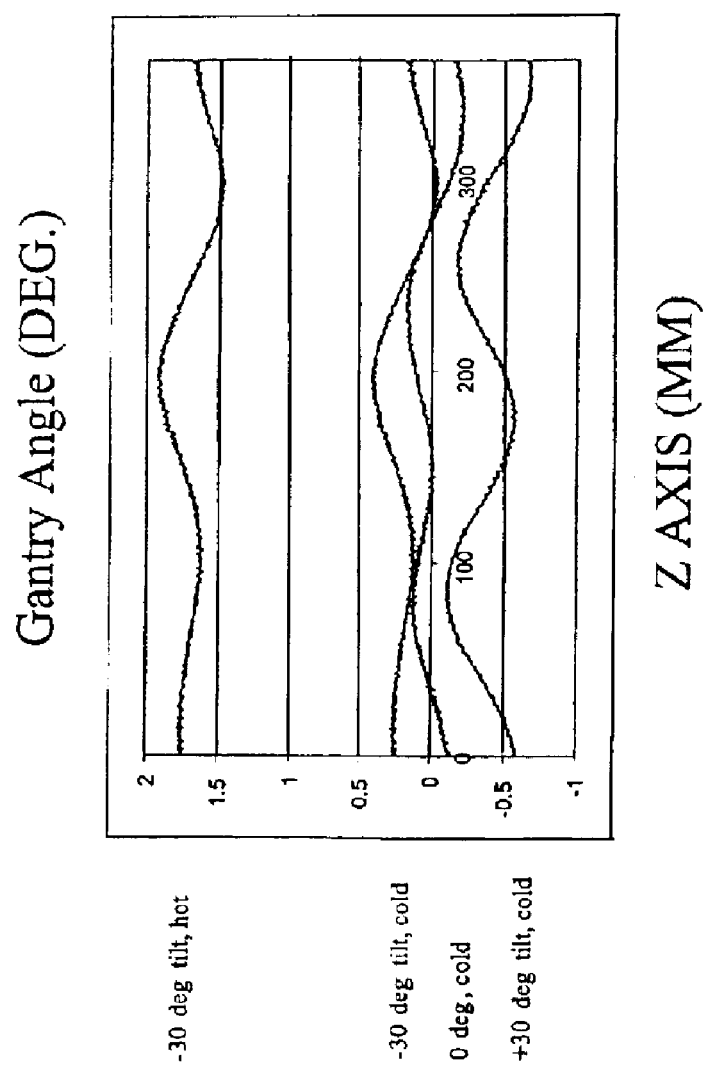
FIG. 3 illustrates examples of beam movement in the Z axis as a function of gantry angle and temperature.

Herein described are methods to characterize gantry motions relative to scan space 23 and CT image reconstruction methods to correct for view dependent X, Y, and Z sample position errors such as those shown in FIG. 3. FIG. 3 illustrates some typical examples of beam movement in the Z axis as a function of gantry angle and temperature.

Figure 4:
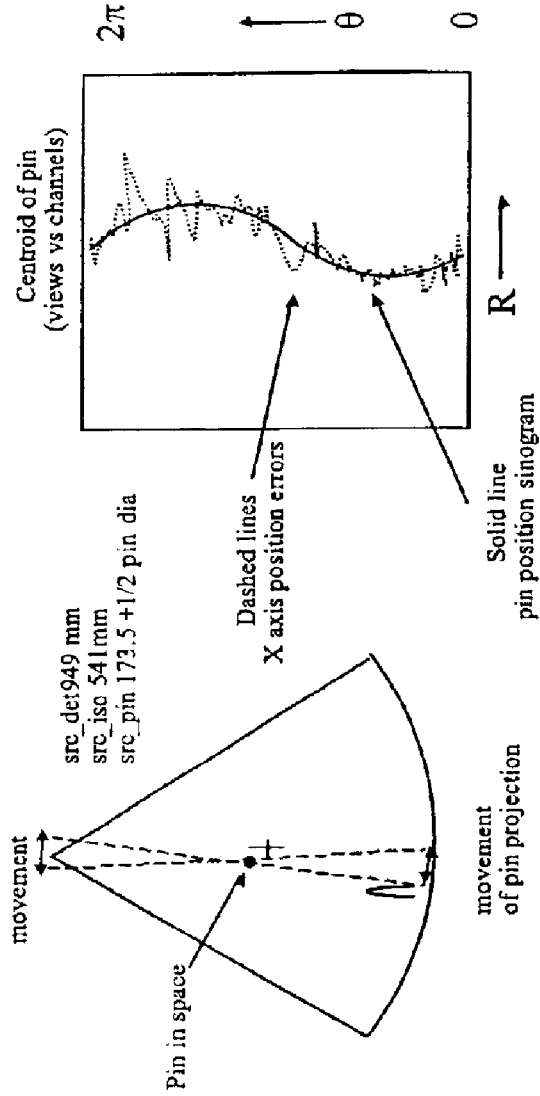
FIG. 4 illustrates a pin position sinogram and a measured centroid.

X axis errors in the projections are measured for various gantry conditions of operation (i.e., operating parameters such as temperature (e.g., hot, cold,), speed, and tilt angle) by scanning a pin in scan space 23 and computing a centroid as a function of view angle. The centroid of the pin minus a pin position sinogram (1 cycle and constant terms) indicates the position error of the ray relative to the pin fixed in space as a function of gantry angle and system geometry. FIG. 4 illustrates a solid line 60 representing a sinogram for the pin position and a dashed line 62 representing the centroid. The distance between dashed line 62 and solid line 60 represents X axis position errors.

The view angle dependent variations (errors) are stored in a calibration database. During patient scanning, the stored position variations associated with the conditions of operation are applied during image reconstruction to compensate for angle dependent X axis position errors in a manner, for example, similar to that described by Toth in U.S. Pat. No. 6,185,275 assigned to the assignee of the instant invention and which is hereby incorporated by reference in its entirety for all purposes.

Figure 5:
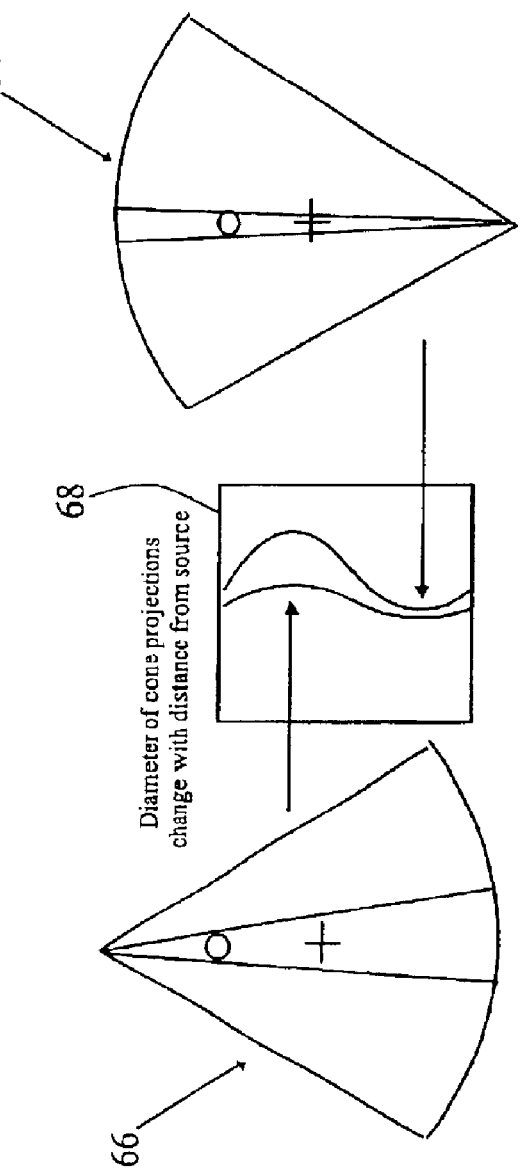
FIG. 5 includes a sinogram illustrating measured differences in diameter.

Additionally Z axis position errors relative to an object in space are measured for various gantry conditions of operation (operating parameters such as hot, cold, speed, and tilt angle) by scanning a cone object. For example, the cone of a solid uniform material such as Teflon with a unity slope is scanned while positioned substantially exactly at isocenter. If the beam position were to remain constant in Z, then the projected cone diameter where intersected by the beam will be a constant in every view. If the position of the beam moves in Z, then the diameter of the projected cone will increase or decrease proportionally to the Z movement in accordance with the system geometry. FIG. 5 illustrates a small measured diameter 64 at one position in Z and a large measured diameter 66 at another position in Z. FIG. 5 includes a sinogram 68 illustrating the measured differences in diameter. Hence the Z position error of each projection is determined for the sample plane at isocenter.

Figure 6:
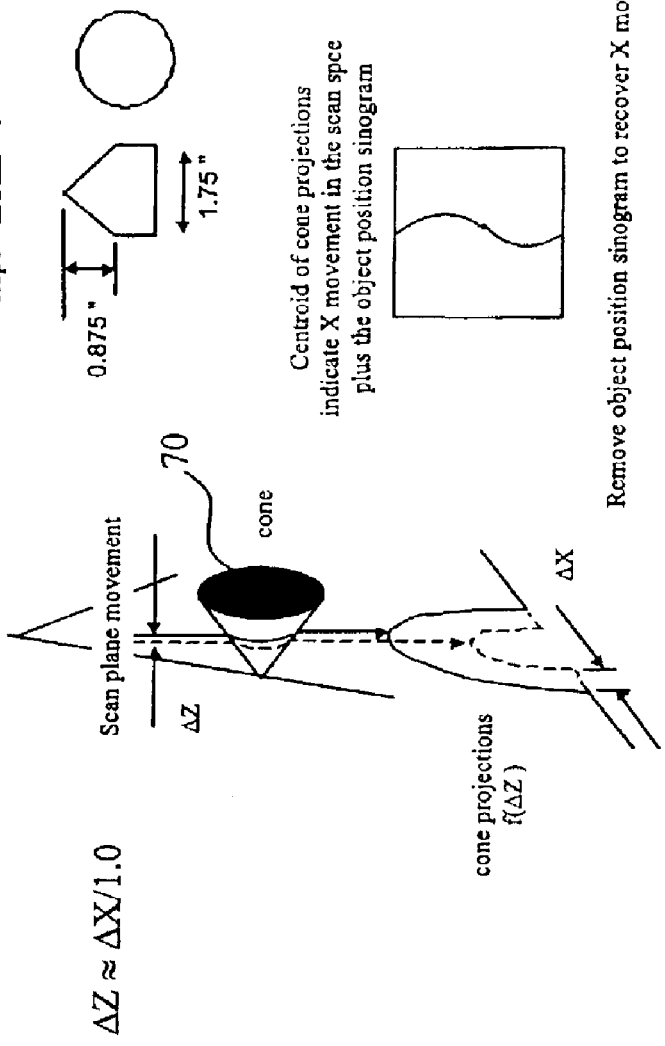
FIG. 6 illustrates the obtainment of the Z position errors illustrated in FIG. 5.

FIG. 6 illustrates the obtainment of the Z position error illustrated in FIG. 5. Since the gantry rotates in a plane, one wants to measure Z-axis movement for at least three different points of the scan plane. One can do this by scanning a cone 70 while it is positioned at a radial distance away from isocenter (about 100 mm for example). Since the projected diameter of cone 70 is dependent on (1) its radial position, (2) the view angle, and (3) system geometry, one can compute an expected projected cone diameter. The position of cone 70 in the scan space is obtained from the scan data by computing the centroid. The Z position error as a function of view angle is then obtained from the change in projected cone diameter relative to the expected diameter as for the isocenter case.

The Z position movement of the plane as function of gantry angle is characterized for various conditions of operation and stored in a calibration data base. During patient scanning, the stored position variations associated with the conditions of operation are applied during image reconstruction to compensate for Z position errors. Image artifacts and Z resolution are improved by using the true position of the data in the helical, cone beam or other multislice reconstruction algorithm.

For example, with a simple helical interpolation algorithm, projection values for the desired image plane are interpolated from the true Z position of the data instead of at the expected nominal position. This results in significant improvements to Z resolution and artifacts since scan plane movement in Z of up 0.3 mm are possible at narrow slices (0.5 mm) when high gantry scan speeds are used (0.5 sec).

Exemplary embodiments of methods, systems, computers, product lines, and computer readable medium for facilitating a reduction in image artifacts are described above in detail. The methods, systems, computers, product lines, and computer readable medium are not limited to the specific embodiments described herein, but rather, components of each methods, systems, computers, product lines, and computer readable medium may be utilized independently and separately from other components described herein. In addition, each methods, systems, computers, product lines, and computer readable medium component can also be used in combination with other components described herein.

While the invention has been described in terms of various specific embodiments, those skilled in the art will recognize that the invention can be practiced with modification within the spirit and scope of the claims.

What is claimed is:

1. A method for facilitating a reduction in image artifacts, said method comprising:
   determining at least one error due to motion of an imaging system relative to a scan space;
   scanning an object to acquire data with the imaging system; and
   correcting the acquired data using the determined error.

2. A method in accordance with claim 1 wherein said determining at least one error comprises determining at least one error due to motion in an X direction by:
   scanning a pin positioned within the scan space; and
   computing a centroid of the pin as a function of gantry angle.

3. A method in accordance with claim 2 further comprising comparing the computed centroid with a pin position sinogram to determine error as a function of gantry angle and imaging system geometry.

4. A method in accordance with claim 3 wherein said comparing the computed centroid with a pin position sinogram comprises comparing the computed centroid with a pin position sinogram to determine error as a function of gantry angle and imaging system geometry, wherein the system comprises a Computed Tomography (CT) imaging system.

5. A method in accordance with claim 1 wherein said determining at least one error comprises determining at least one error due to motion in a Z direction by:
   scanning a substantially cone shaped object comprising a substantially homogeneous material;
   computing an expected cone diameter; and
   comparing an obtained cone diameter with the computed expected cone diameter to determine error in the Z direction.

6. A method in accordance with claim 5 wherein said comparing an obtained cone diameter comprises comparing the obtained cone diameter with the computed expected cone diameter to determine error in the Z direction as a function of gantry angle.

7. A method in accordance with claim 1 wherein said determining at least one error due to motion of an imaging system relative to a scan space comprises:
   determining at least one error due to motion of the imaging system relative to the scan space in an X direction; and
   determining at least one error due to motion of the imaging system relative to the scan space in a Z direction.

8. A method in accordance with claim 7 wherein said determining at least one error due to motion of the imaging system relative to the X direction comprises:
   scanning a pin positioned within the scan space; and
   computing a centroid of the pin as a function of gantry angle;
   said determining at least one error due to motion of the imaging system relative to the Z direction comprises:
      scanning a substantially cone shaped object having a substantially unitary slope and comprising a substantially homogeneous material; and
      comparing an obtained cone diameter with a computed expected cone diameter to determine error in the Z direction.

9. A method in accordance with claim 8 further comprising:
   comparing the computed centroid with a pin position sinogram to determine error in the X direction as a function of gantry angle and imaging system geometry; and
   comparing the obtained cone diameter with the computed expected cone diameter to determine error in the Z direction as a function of gantry angle.

10. A method in accordance with claim 1 wherein said determining comprises determining a plurality of errors associated with at least one operating parameter including at least one of a temperature, a view angle, and a Z position, said method further comprising:
   storing the determined errors according to each error's associated operating parameter;
   determining a current status of the operating parameter during the scan; and
   retrieving the stored errors associated with the determined current status of the operating parameter.

11. An imaging system comprising:
   a radiation source;
   a radiation detector positioned to define a scan space between said detector and said source; and
   a computer operationally coupled to said radiation source and said radiation detector, said computer configured to:
   scan an object to acquire data;
   determine a current status of at least one operating parameter including at least one of a temperature, a gantry angle, and a Z-position during the scan; and
   correct the acquired data for motion relative to a scan space using the determined current status of the operating parameter.

12. A system in accordance with claim 11 wherein said computer further configured to:
   determine current statuses of a plurality of operating parameters including the temperature, the gantry angle, and the Z-position during the scan; and
   correct the acquired data for motion relative to the scan space using the determined current statuses.

13. A system in accordance with claim 11 wherein said computer further configured to correct the acquired data for motion relative to the scan space using the determined current statuses by using stored errors according to gantry angle and imaging system geometry determined by comparing a computed centroid with a pin position sinogram.

14. A system in accordance with claim 11 wherein said system comprises a Computed Tomography (CT) system.

15. A system in accordance with claim 11 wherein said computer further configured to correct the acquired data for motion relative to the scan space using the determined current statuses by using stored Z direction errors determined by comparing an obtained cone diameter with an expected cone diameter.

16. A product line of imaging systems comprising a plurality of imaging systems each comprising a radiation detector, a radiation source positioned to define a scan space between said detector and said source, and a computer operationally coupled to said detector and said source, each imaging system configured to correct for motion relative to the scan space using stored errors particular to that imaging system.

17. A product line in accordance with claim 16 wherein each imaging system configured to correct acquired data for motion relative to the scan space using stored errors particular to that imaging system determined by comparing a computed centroid with a pin position sinogram.

18. A product line in accordance with claim 16 wherein each imaging system configured to correct acquired data for motion relative to the scan space using stored errors particular to that imaging system determined by comparing an obtained cone diameter with an expected cone diameter.

19. A product line in accordance with claim 16 wherein each imaging system configured to correct acquired data for motion relative to the scan space using stored X direction errors particular to that imaging system determined by comparing a computed centroid with a pin position sinogram and using stored Z direction errors particular to that imaging system determined by comparing an obtained cone diameter with an expected cone diameter.

20. A product line in accordance with claim 19 wherein said imaging systems each comprise a memory wherein the stored errors are associated with a plurality of operating parameters including a temperature, a gantry angle, and a Z-position, said computer further configured to:
   scan an object to acquire data; and
   determine the current status of the operating parameters during the scan; and
   retrieve the stored errors associated with the determined current status.

21. A computer configured to:
   scan an object to acquire data; and
   determine a current status of at least one operating parameter including at least one of a temperature, a gantry angle, and a Z-position during the scan; and
   correct the acquired data for motion relative to a scan space using the determined current status.

22. A computer in accordance with claim 21 further configured to:
   determine current statuses of a plurality of operating parameters including the temperature, the gantry angle, and the Z-position during the scan; and
   correct the acquired data for motion relative to the scan space using the determined current statuses.

23. A computer in accordance with claim 22 further configured to correct the acquired data for motion relative to the scan space using the determined current statuses by using stored errors according to gantry angle and imaging system geometry determined by comparing a computed centroid with a pin position sinogram.

24. A computer in accordance with claim 22 further configured to correct the acquired data for motion relative to the scan space using the determined current statuses by using stored Z direction errors determined by comparing an obtained cone diameter with an expected cone diameter.

25. A computer readable medium encoded with a program configured to instruct a computer to:

determine a current status of at least one operating parameter of an imaging system including at least one of a temperature, a gantry angle, and a Z-position during a scan which acquires data; and correct the acquired data for motion relative to a scan space using the determined current status.

26. A method for determining misalignment, said method comprising:

determining at least one error due to motion of an imaging system relative to a scan space;

comparing the determined error to a reference error value; and providing an indication of misalignment when the determined error exceeds the reference value.

27. A method in accordance with claim 26 further comprising servicing the imaging system to decrease error due to motion of the imaging system relative to the scan space.

28. A method in accordance with claim 27 further comprising re-balancing a gantry of the imaging system.

* * * * *